United States Patent
Sturgis et al.

(10) Patent No.: US 11,090,235 B2
(45) Date of Patent: *Aug. 17, 2021

(54) ANTIPERSPIRANT COMPOSITIONS AND METHODS

(71) Applicant: The Procter & Gamble Company, Cincinnati, OH (US)

(72) Inventors: David Arthur Sturgis, Cincinnati, OH (US); Steven Michael Wujek, Sr., Loveland, OH (US); Phi Van Chu, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 508 days.

This patent is subject to a terminal disclaimer.

(21) Appl. No.: 13/956,744

(22) Filed: Aug. 1, 2013

(65) Prior Publication Data

US 2014/0037567 A1 Feb. 6, 2014

Related U.S. Application Data

(60) Provisional application No. 61/678,642, filed on Aug. 2, 2012.

(51) Int. Cl.
*A61K 8/18* (2006.01)
*A61Q 15/00* (2006.01)
*A61K 8/73* (2006.01)
*A61K 8/58* (2006.01)
*A61K 8/25* (2006.01)

(52) U.S. Cl.
CPC .............. *A61K 8/18* (2013.01); *A61K 8/25* (2013.01); *A61K 8/585* (2013.01); *A61K 8/738* (2013.01); *A61Q 15/00* (2013.01)

(58) Field of Classification Search
None
See application file for complete search history.

(56) References Cited

U.S. PATENT DOCUMENTS

| | | |
|---|---|---|
| 3,792,068 A | 2/1974 | Luedders et al. |
| 3,887,692 A | 6/1975 | Gilman |
| 3,904,741 A | 9/1975 | Jones et al. |
| 4,049,792 A | 9/1977 | Elsnau |
| 4,120,948 A | 10/1978 | Shelton |
| 4,359,456 A | 11/1982 | Gosling et al. |
| 5,019,375 A | 5/1991 | Tanner et al. |
| 5,225,188 A | 7/1993 | Abrutyn et al. |
| 5,281,413 A | 1/1994 | Abrutyn et al. |
| 5,302,381 A | 4/1994 | Greczyn et al. |
| 5,354,553 A | 10/1994 | Greczyn et al. |
| 5,378,452 A | 1/1995 | Greczyn |
| 5,417,964 A | 5/1995 | Carlson, Sr. et al. |
| 5,429,816 A | 7/1995 | Hofrichter et al. |
| 5,486,355 A | 1/1996 | Berschied, Jr. |
| 5,631,013 A | 5/1997 | Bergmann et al. |
| 5,707,613 A | 1/1998 | Hill |
| 5,733,534 A | 3/1998 | Sawin et al. |
| 5,744,130 A | 4/1998 | Guskey et al. |
| 5,750,096 A | 5/1998 | Guskey |
| 5,756,082 A | 5/1998 | Cashin et al. |
| 5,833,964 A | 11/1998 | Linn et al. |
| 5,840,286 A | 11/1998 | Gardlik et al. |
| 5,846,520 A | 12/1998 | Guskey et al. |
| 5,849,276 A | 12/1998 | Guskey et al. |
| 5,891,424 A | 4/1999 | Bretzler et al. |
| 5,976,514 A | 11/1999 | Guskey et al. |
| 6,007,799 A | 12/1999 | Lee et al. |
| 6,045,823 A | 4/2000 | Vollhardt et al. |
| 6,103,250 A | 8/2000 | Brieva et al. |
| 6,350,460 B1 | 2/2002 | Andrews et al. |
| 6,352,688 B1 | 3/2002 | Scavone et al. |
| 6,361,765 B1 | 3/2002 | Emslie et al. |
| 6,361,766 B1 | 3/2002 | Franklin et al. |
| 6,387,358 B2 | 5/2002 | Chuah et al. |
| 6,428,777 B1 | 8/2002 | Boyle et al. |
| 6,458,345 B1 | 10/2002 | Emslie et al. |
| 6,485,732 B1 | 11/2002 | Bekele |
| 6,488,919 B1 | 12/2002 | Murphy et al. |
| 6,555,509 B2 | 4/2003 | Abbas et al. |
| 6,682,749 B1 | 1/2004 | Potechin et al. |
| 6,960,339 B1 | 11/2005 | Ferrari |
| 7,005,557 B2 | 2/2006 | Klofta et al. |
| 7,037,511 B1 | 5/2006 | Gers-Barlag et al. |
| 7,250,159 B1 | 7/2007 | Arnaud |
| 7,270,828 B2 | 9/2007 | Masuda et al. |
| 7,347,989 B2 * | 3/2008 | Walling ............... A61K 8/0229 424/400 |
| 7,413,744 B2 | 8/2008 | Ichinohe |
| 7,449,613 B2 | 11/2008 | Klofta et al. |
| 7,678,381 B2 | 3/2010 | Lupia et al. |
| 7,709,015 B2 | 5/2010 | Masuda et al. |
| 7,713,520 B2 | 5/2010 | Sakuta |
| 8,048,406 B2 | 11/2011 | Galante et al. |
| 8,258,248 B2 | 9/2012 | Jennings et al. |
| 8,449,868 B2 | 5/2013 | Jennings et al. |
| 9,717,930 B2 * | 8/2017 | Sturgis .................. A61Q 15/00 |
| 9,937,113 B2 * | 4/2018 | Sturgis .................... A61K 8/28 |
| 2001/0003586 A1 | 6/2001 | Vatter et al. |
| 2002/0034481 A1 | 3/2002 | Bianchi et al. |

(Continued)

FOREIGN PATENT DOCUMENTS

| | | |
|---|---|---|
| BE | 825146 A | 8/1975 |
| GB | 1 347 950 | 2/1974 |

(Continued)

OTHER PUBLICATIONS

Scientific Committee on Consumer Safety (SCCS) Opinion on Cyclomethicone. pp. 1-103. publication date: Jun. 22, 2010.*

(Continued)

*Primary Examiner* — Katherine Peebles (74) *Attorney, Agent, or Firm* — Kathleen Y. Carter (57) ABSTRACT

Achieving enhanced scent expression in antiperspirant compositions and methods.

11 Claims, 4 Drawing Sheets

(56) References Cited

U.S. PATENT DOCUMENTS

| | | |
|---|---|---|
| 2002/0037993 A1 | 3/2002 | Lawson et al. |
| 2002/0071817 A1 | 6/2002 | Rizvi et al. |
| 2002/0081272 A1 | 6/2002 | Guenin et al. |
| 2002/0119108 A1 | 8/2002 | Rieley et al. |
| 2002/0150602 A1 | 10/2002 | Livoreil et al. |
| 2002/0182233 A1 | 12/2002 | Ambler et al. |
| 2003/0021756 A1 | 1/2003 | Ferrari |
| 2003/0118621 A1 | 6/2003 | Heidenfelder et al. |
| 2003/0152539 A1 | 8/2003 | Scavone et al. |
| 2003/0199405 A1 | 10/2003 | Abbas et al. |
| 2003/0202949 A1 | 10/2003 | Abrutyn |
| 2003/0211060 A1 | 11/2003 | Yin et al. |
| 2003/0235545 A1 | 12/2003 | Guenin et al. |
| 2004/0028641 A1 | 2/2004 | Barone et al. |
| 2004/0096408 A1 | 5/2004 | Elliott et al. |
| 2005/0112072 A1 | 5/2005 | Wang et al. |
| 2005/0249690 A1 | 11/2005 | Rojas-Wahl et al. |
| 2005/0287069 A1 | 12/2005 | Walling et al. |
| 2006/0029624 A1 | 2/2006 | Banowski et al. |
| 2006/0171973 A1 | 8/2006 | Witham et al. |
| 2007/0059263 A1 | 3/2007 | Taniguchi et al. |
| 2007/0060666 A1 | 3/2007 | Taniguchi et al. |
| 2007/0092541 A1 | 4/2007 | Walling et al. |
| 2007/0116662 A1 | 5/2007 | Zielinski et al. |
| 2007/0248552 A1 | 10/2007 | Scavone et al. |
| 2007/0253922 A1 | 11/2007 | Taira |
| 2007/0254039 A1 | 11/2007 | Witham et al. |
| 2008/0063616 A1 | 3/2008 | Walling et al. |
| 2008/0187504 A1* | 8/2008 | Fan et al. ............... 424/65 |
| 2008/0213204 A1* | 9/2008 | Scavone et al. ............... 424/65 |
| 2008/0241089 A1 | 10/2008 | Banowski et al. |
| 2008/0317686 A1 | 12/2008 | Mateu et al. |
| 2009/0010864 A1 | 1/2009 | Banowski et al. |
| 2009/0304617 A1 | 12/2009 | Banowski et al. |
| 2010/0047296 A1 | 2/2010 | Banowski et al. |
| 2010/0112022 A1 | 5/2010 | Hoying et al. |
| 2010/0143278 A1 | 6/2010 | Banowski et al. |
| 2011/0076309 A1 | 3/2011 | Misner et al. |
| 2011/0076310 A1 | 3/2011 | Fan et al. |
| 2011/0212144 A1 | 9/2011 | Lemoine et al. |
| 2011/0274637 A1 | 11/2011 | Milardovic et al. |
| 2012/0070393 A1 | 3/2012 | Mateu et al. |
| 2012/0114582 A1 | 5/2012 | Batchelor et al. |
| 2012/0121737 A1 | 5/2012 | Vielhaber et al. |

FOREIGN PATENT DOCUMENTS

| | | |
|---|---|---|
| GB | 2 048 229 A | 12/1980 |
| GB | 2 144 992 A | 3/1985 |
| GB | 2 299 024 A | 9/1996 |
| WO | 02/087516 A2 | 11/2002 |
| WO | WO 2010/072705 * | 7/2010 |
| WO | 2010/089314 A1 | 8/2010 |

OTHER PUBLICATIONS

Hansen, CM. Hansen Solubility Parameters—A User's Handbook. Table of Contents and Chapter 1. pp. 1-32. Publication year 1999.*
Engish Machine Translation of Banowski WO 2010/072705 [online]. Retrieved from the internet: <www.espacenet.com>. Retrieved on: Aug. 16, 2018.*
Todd et al., "Volatile Silicone Fluids for Cosmetics", Cosmetic and Toiletries, 91:27-32 (1976).

* cited by examiner

ANTIPERSPIRANT COMPOSITIONS AND METHODS

FIELD OF THE INVENTION

The present disclosure relates to antiperspirant compositions and methods relating thereto.

BACKGROUND OF THE INVENTION

There are many factors that contribute to the purchase intent of a consumer when looking for a deodorant or antiperspirant products, like the expected or previously experienced odor and wetness protection, residue, and skin feel. One of the often overlooked purchase intent drivers is scent. When formulating products, a balance is often struck between performance and other properties which encourage purchase. Scent is one of the purchase encouraging properties often sacrificed for performance. Thus, there is a need for deodorant and antiperspirant products that have better fragrance expression.

SUMMARY OF THE INVENTION

A method of enhancing fragrance expression, comprising formulating an antiperspirant composition so that no more than 25% by weight of the composition, of the non-perfume and non-antiperspirant active ingredients, have a polarity between 3 MPa$^{1/2}$ and 15 MPa$^{1/2}$.

A method of enhancing fragrance expression in a solid antiperspirant product, comprising formulating an antiperspirant composition comprising about 7% to about 20% of a primary structurant; about 10 to about 25% of an antiperspirant active; a perfume; and additional chassis ingredients; wherein about 15% or less, by weight of the composition, of the additional chassis ingredients have a polarity greater than about 3.0 MPa$^{1/2}$.

DETAILED DESCRIPTION OF THE INVENTION

This application claims priority to U.S. Provisional App. No. 61/678,642 filed Aug. 2, 2012 which is incorporated herein by reference.

The term "anhydrous" as used herein means substantially free of added or free water. From a formulation standpoint, this means that the anhydrous antiperspirant stick compositions of the present invention contain less than about 1%, and more specifically zero percent, by weight of free or added water, other than the water of hydration typically associated with the particulate antiperspirant active prior to formulation.

The term "ambient conditions" as used herein refers to surrounding conditions under about one atmosphere of pressure, at about 50% relative humidity, and at about 25° C., unless otherwise specified. All values, amounts, and measurements described herein are obtained under ambient conditions unless otherwise specified.

The term "majority" refers to greater than about 51% of the stated component or parameter.

The term "polarity" as used herein is defined by the Hansen Solubility Parameter for solubility.

"Substantially free of" refers to about 2% or less, about 1% or less, or about 0.1% or less of a stated ingredient. "Free of" refers to no detectable amount of the stated ingredient or thing.

The term "volatile" as used herein refers to those materials that have a measurable vapor pressure at 25° C. Such vapor pressures typically range from about 0.01 millimeters of Mercury (mm Hg) to about 6 mmHg, more typically from about 0.02 mmHg to about 1.5 mmHg; and have an average boiling point at one (1) atmosphere of pressure of less than about 250° C., more typically less than about 235° C. Conversely, the term "non-volatile" refers to those materials that are not "volatile" as defined herein.

All percentages, parts and ratios are by weight of the total composition, unless otherwise specified. All such weights as they pertain to the listed ingredients are based on the specific ingredient level and, therefore, do not include solvents, carriers, by-products, filler or other minor ingredients that may be included in commercially available materials, unless otherwise specified.

When looking at currently marketed invisible solid antiperspirant products, consumers will often rank the performance of a product by attribute. Unsurprisingly, invisible solid products often get midland to low scores on scent expression. This is due, at least in part, to the trapping of fragrance materials within the composition so that they are not sufficiently expressed at application.

Products in the solid form tend to use more wax than other forms of antiperspirant and deodorant, like soft solid, in order to attain the desired product hardness that is the signature of the solid form. The downsides to larger amounts of wax include cost, whiteness in appearance on skin, and a feeling of waxy residue after application. To reduce these negative attributes of wax, other materials are added to the formulation and these materials often have negative effects on perfume expression. Additionally, the amount of wax itself appears to have an impact on perfume expression.

Without being limited by theory, the present inventors believe that by modifying a formulation to limit the overlap of the polarity of chassis ingredients with those in a perfume, the resulting product will have a better scent expression. See, for example, FIG. 1 which shows an overlap in polarity between some of the product ingredients and some of the perfume raw materials and FIG. 2 which shows how reformulating the product (Inventive Formulation 1) minimizes the overlap between the product ingredients and the perfume raw materials. When these two formulations were compared head-to-head, Table A, below, shows the significant wins for Inventive Formulation 1 in both fragrance at application and scent liking at application. Comparative Formulation 1 and Inventive Formulation 1 both contained the same perfume at the same level.

TABLE A

|  | Comparative Formula #1 | Inventive Formula #1 |
|---|---|---|
| Fragrance at Application | 6.32 | 6.91 |
| Scent Liking at Application | 6.8 | 7.15 |

Moreover, there was also an efficacy boost in wetness as seen in Table B, below.

TABLE B

| | Analysis of Sweat Amount - Treatment Estimates | | | | | |
|---|---|---|---|---|---|---|
| | Baseline | | Day 5 | | Day 10 | |
| Treatment | [N] Mean (SE) | Sweat (mg) | [N] Mean (SE) | Sweat (mg) | [N] Mean (SE) | Sweat (mg) |
| [C] Comparative Formula #1 | [28] 2.71 (0.024) | 508 | [28] 2.43 (0.028) | 267 (47%) | [28] 2.42 (0.027) | 263 (48%) |
| [D] Inventive Formula #1 | [28] 2.71 (0.024) | 509 | [28] 2.41 (0.028) | 255 (50%) | [28] 2.37 (0.027) | 237 (53%) |

When looking to quantify the formulation attributes that would lead to a better scent expressing product, several avenues are identified. The first is a maximum total percentage of non-perfume and non-antiperspirant ingredients within a composition that can have a polarity value between 3 $MPa^{1/2}$ and 15 $MPa^{1/2}$. In other words, one would look at the total of all ingredients, excluding perfumes and antiperspirants, with a polarity value between 3 $MPa^{1/2}$ and 10 $MPa^{1/2}$ and the percentage of those ingredients can be 25% or less, although some formulations may be even lower at, for example, 23%, 20, 17, 15, 12, 10, 8, 6, 4, 3, or 2%, or less.

There are some non-perfume, non-antiperspirant components which appear to have a larger impact on perfume expression. Some of these components have a polarity of 15 $MPa^{1/2}$ or more, like castor wax. Thus, when looking at the maximum total percentage parameter, there are occasions, when those ingredients with a polarity of 15 $MPa^{1/2}$ or more may be formulated at an amount of about 4%, 3, 2, or 1%, or less. The composition may be substantially free of or free of castor wax. The composition may also be free of non-perfume and non-antiperspirant ingredients with a polarity of 10 $MPa^{1/2}$ or more.

Another option for attaining better fragrance expression is through the control of the polarity of certain ingredients in the composition. For example, an antiperspirant composition often has a primary structurant, an antiperspirant active, a perfume, optional ingredients, and then additional chassis ingredients like an additional structurant, a solvent, and/or a non-volatile organic fluid. The limitation of polarity on the additional chassis ingredients can also help perfume expression. This is seen, for example, where the composition contains 10% or less, by weight of the composition, of additional chassis materials with a polarity that overlaps with the majority of the majority of the perfume raw materials by 50% or more. Some formulations may be even lower and comprise 9%, 8, 7, 6, 5, 4, or 3%, or less, by weight of the composition, of additional chassis ingredients with a polarity overlapping the majority of perfume raw materials by 50% or more. The composition may be substantially free of or free of castor wax.

A third option for attaining better fragrance expression is through the control of the polarity of additional chassis materials by limiting the maximum amount of additional chassis materials that can have a polarity of 3.0 $MPa^{1/2}$ or more to 15% or less by weight of the composition. Some formulations may have even less and comprise 12%, 10, 8, 6, 5, 4, or 3%, or less, by weight of the composition, of additional chassis materials that have a polarity of 3.0 $MPa^{1/2}$ or more.

Figure 1:
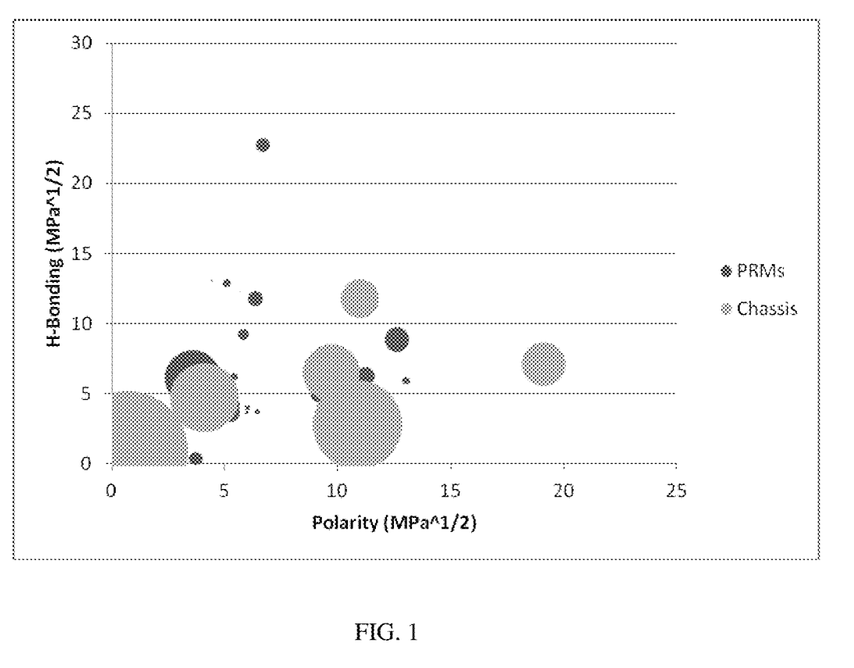
FIG. 1 is a graph depicting the polarity (x-axis) and hydrogen bonding (y-axis) of chassis ingredients and perfume raw materials in a currently marketed product.
Figure 2:
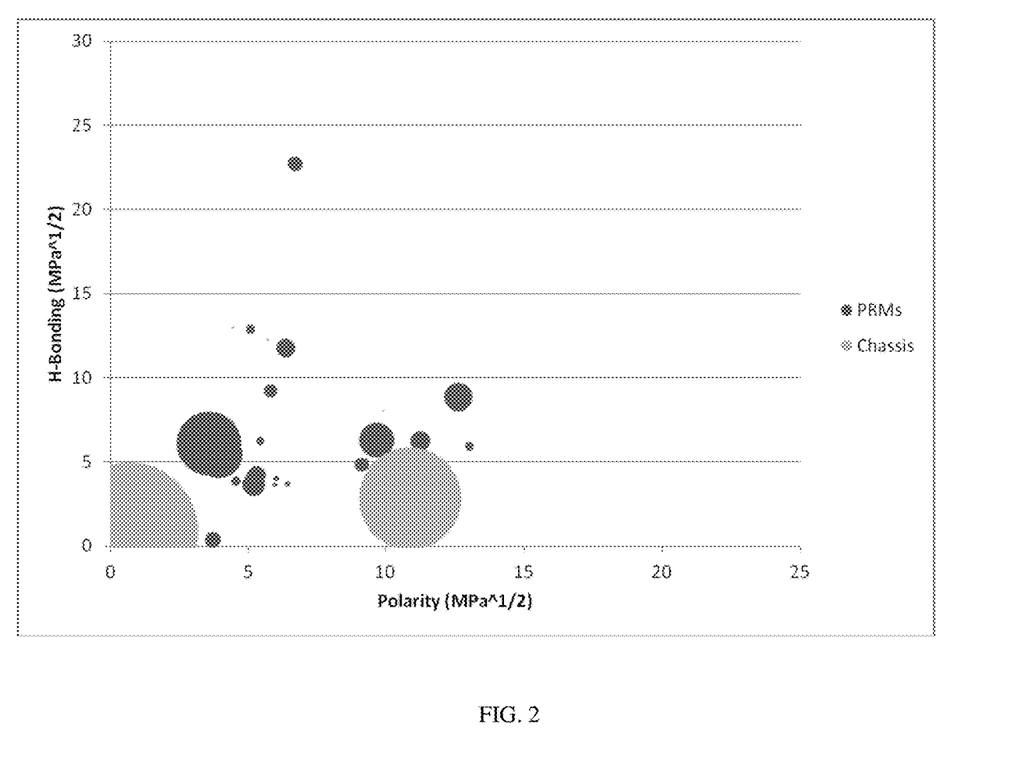
FIG. 2 is a graph depicting the polarity (x-axis) and hydrogen bonding (y-axis) of chassis ingredients and perfume raw materials when formulated as described herein.
Figure 3:
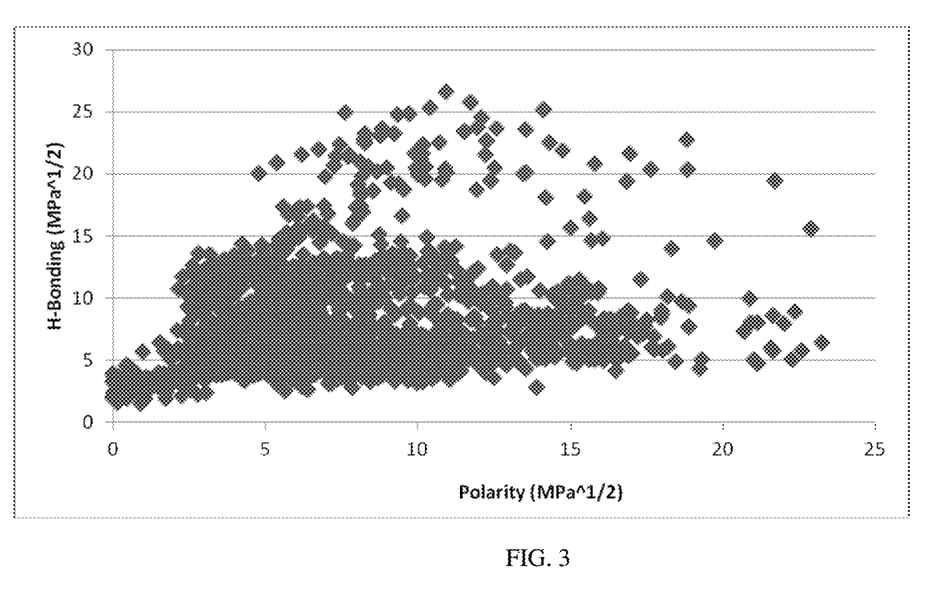
FIG. 3 is a graph depicting the polarity (x-axis) and hydrogen bonding (y-axis) of a variety of perfume raw materials.

Another parameter that can be helpful to formulate antiperspirant products with better scent expression is hydrogen bonding (H-bonding), as seen in FIGS. 1-3. As polarity increases, hydrogen bonding also naturally increases making it harder to prevent overlap of perfume raw materials and other ingredients, especially when the polarity increases beyond 3.0 $MPa^{1/2}$. Thus, it is also helpful to limit the components with H-bonding between about 3.0 $MPa^{1/2}$ and about 10 $MPa^{1/2}$ to less than about 25%. As seen in FIG. 2, there are many more options of materials with a H-bonding below 4 $MPa^{1/2}$, when you go below a polarity of 3 $MPa^{1/2}$.

Figure 4:
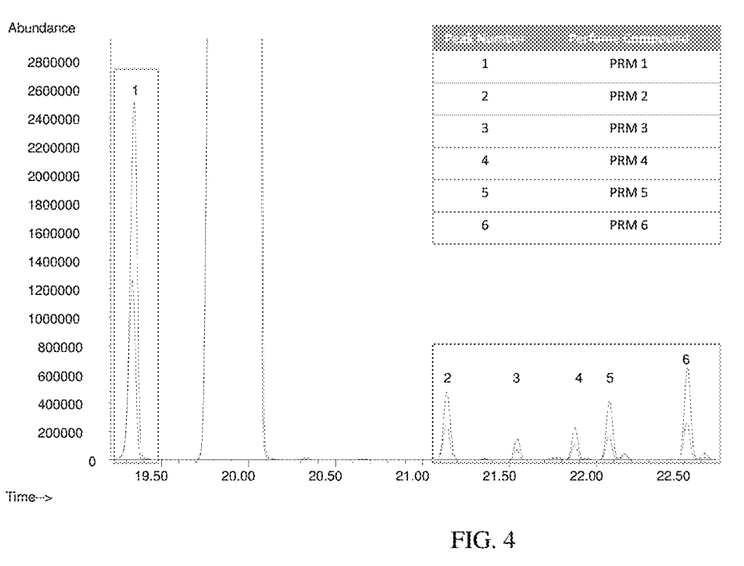
FIG. 4 is a chromatogram overlay from a headspace gas chromatography.

Moreover, further support for the fragrance expression benefits of formulating a composition according to the teachings here can be seen in FIG. 4. In FIG. 4, headspace gas chromatography was run on Comparative Example 1(red/lower graph) and Inventive Example 5 (blue/upper graph). As can be seen from FIG. 4, for the six perfume raw materials (PRM's) measured, Inventive Example 5 displayed a significantly higher amount of fragrance in the head space than that of Comparative Example 1. The average ratio across the PRM's expressed in the inventive formula versus the comparative formula was 1.7.

Any of these options may be combined in any combination to help formulate for enhanced scent expression.

Antiperspirant Composition

The antiperspirant compositions as described herein can contain a primary structurant, an antiperspirant active, a perfume, and additional chassis ingredient(s). The antiperspirant composition may further comprise other optional ingredient(s). The compositions can be in the form of a solid stick. The compositions can have a product hardness of about 600 gram force or more. The compositions may be free of dipropylene glycol, added water, castor wax, or any combination thereof. The antiperspirant composition may be anhydrous. The antiperspirant composition may be free of added water.

Hardness

The antiperspirant compositions of the present invention can have a product hardness of least about 600 gram·force, more specifically from about 600 gram·force to about 5,000 gram·force, still more specifically from about 750 gram·force to about 2,000 gram·force, and yet more specifically from about 800 gram·force to about 1,400 gram·force.

The term "product hardness" or "hardness" as used herein is a reflection of how much force is required to move a penetration cone a specified distance and at a controlled rate into an antiperspirant composition under the test conditions described herein below. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the peak force required to move a standard 45-degree angle penetration cone through the composition for a distance of 10 mm at a speed of 2 mm/second. The standard cone is available from Texture Technology Corp., as part number TA-15, and has a total cone length of about 24.7 mm, angled cone length of about 18.3 mm, and a maximum diameter of the angled surface of the cone of about 15.5 mm. The cone is a smooth, stainless steel construction and weighs about 17.8 grams.

Primary Structurants

The antiperspirant compositions of the present invention comprise a suitable concentration of a primary structurant to help provide the compositions with the desired viscosity, rheology, texture and/or product hardness, or to otherwise help suspend any dispersed solids or liquids within the composition.

The term "solid structurant" as used herein means any material known or otherwise effective in providing suspending, gelling, viscosifying, solidifying, and/or thickening properties to the composition or which otherwise provide structure to the final product form. These solid structurants include gelling agents, and polymeric or non-polymeric or inorganic thickening or viscosifying agents. Such materials will typically be solids under ambient conditions and include organic solids, crystalline or other gellants, inorganic particulates such as clays or silicas, or combinations thereof.

The concentration and type of solid structurant selected for use in the antiperspirant compositions will vary depending upon the desired product hardness, rheology, and/or other related product characteristics. For most structurants suitable for use herein, the total structurant concentration ranges from about 5% to about 35%, more typically from about 10% to about 30%, or from about 7% to about 20%, by weight of the composition.

Non-limiting examples of suitable primary structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; solid triglycerides; behenyl alcohol, or combinations thereof.

Other non-limiting examples of primary structurants suitable for use herein are described in U.S. Pat. No. 5,976,514 (Guskey et al.) and U.S. Pat. No. 5,891,424 (Bretzler et al.), the descriptions of which are incorporated herein by reference.

Antiperspirant Active

The antiperspirant stick compositions of the present invention can comprise a particulate antiperspirant active suitable for application to human skin. The concentration of antiperspirant active in the composition should be sufficient to provide the desired perspiration wetness and odor control from the antiperspirant stick formulation selected.

The antiperspirant stick compositions of the present invention comprise an antiperspirant active at concentrations of from about 0.5% to about 60%, and more specifically from about 5% to about 35%, by weight of the composition. These weight percentages are calculated on an anhydrous metal salt basis exclusive of water and any complexing agents such as, for example, glycine, and glycine salts. The antiperspirant active as formulated in the composition can be in the form of dispersed particulate solids having an average particle size or equivalent diameter of less than about 100 microns, more specifically less than about 20 microns, and even more specifically less than about 10 microns.

The antiperspirant active for use in the anhydrous antiperspirant compositions of the present invention may include any compound, composition or other material having antiperspirant activity. More specifically, the antiperspirant actives may include astringent metallic salts, especially inorganic and organic salts of aluminum, zirconium and zinc, as well as mixtures thereof. Even more specifically, the antiperspirant actives may include aluminum-containing and/or zirconium-containing salts or materials, such as, for example, aluminum halides, aluminum chlorohydrate, aluminum hydroxyhalides, zirconyl oxyhalides, zirconyl hydroxyhalides, and mixtures thereof.

Aluminum salts for use in the anhydrous antiperspirant stick compositions include those that conform to the formula:

$$Al_2(OH)_a Cl_b \cdot xH_2O,$$

wherein a is from about 2 to about 5;
the sum of a and b is about 6;
x is from about 1 to about 6; and
a, b, and x may have non-integer values.

More specifically, aluminum chlorohydroxides referred to as "5/6 basic chlorohydroxide" may be used, wherein a=5, and "2/3 basic chlorohydroxide", wherein a=4.

Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, the disclosures of which are incorporated herein by reference for the purpose of describing processes for preparing aluminum salts.

Mixtures of aluminum salts are described in British Patent Specification 1,347,950, Shin et al., published Feb. 27, 1974, which description is also incorporated herein by reference.

Zirconium salts for use in the anhydrous antiperspirant stick compositions include those which conform to the formula:

$$ZrO(OH)_{2-a}Cl_a \cdot xH_2O,$$

wherein a is from about 1.5 to about 1.87;
x is from about 1 to about 7; and
a and x may both have non-integer values.

These zirconium salts are described in Belgian Patent 825,146, Schmitz, issued Aug. 4, 1975, which description is incorporated herein by reference. Zirconium salts that additionally contain aluminum and glycine, commonly known as "ZAG complexes," are believed to be especially beneficial. These ZAG complexes contain aluminum chlorohydroxide and zirconyl hydroxy chloride conforming to the above-described formulas. Such ZAG complexes are described in U.S. Pat. No. 3,792,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, disclosures of which are incorporated herein by reference for the limited purpose of describing ZAG complexes.

Also suitable for use herein are enhanced efficacy aluminum-zirconium chlorohydrex-amino acid which typically has the empirical formula $Al_nZr(OH)_{[3n+4-m(n+1)]}(Cl)_{[m(n+1)]}\text{-}AA_q$ where n is 2.0 to 10.0, preferably 3.0 to 8.0; m is about 0.48 to about 1.11 (which corresponds to M:Cl approximately equal to 2.1-0.9), preferably about 0.56 to about 0.83 (which corresponds to M:Cl approximately equal to 1.8-1.2); q is about 0.8 to about 4.0, preferably about 1.0 to 2.0; and AA is an amino acid such as glycine, alanine, valine, serine, leucine, isoleucine, β-alanine, cysteine, β-amino-n-butyric acid, or γ-amino-n-butyric acid, preferably glycine. These salts also generally have some water of hydration associated with them, typically on the order of 1 to 5 moles per mole of salt (typically, about 1% to about 16%, more typically about 4% to about 13% by weight). These salts are generally referred to as aluminum-zirconium trichlorohydrex or tetrachlorohydrex when the Al:Zr ratio is between 2 and 6 and as aluminum-zirconium pentachlorohydrex or octachlorohydrex when the Al:Zr ratio is between 6 and 10. The term "aluminum-zirconium chlorohydrex" is intended to embrace all of these forms. The preferred aluminum-zirconium salt is aluminum-zirconium chlorohydrex-glycine. Additional examples of suitable high efficacy antiperspirant actives can include Aluminum Zirconium Pentachlorohydrex Glycine, Aluminum Zirconium Octachlorohydrex Glycine, or a combination thereof. These high efficacy actives are more fully described in U.S. App. Pub. No. 2007/0003499 by Shen et al. filed Jun. 30, 2005.

Perfume

Perfumes are often a combination of many raw materials, known as perfume raw materials. Any perfume suitable for use in an antiperspirant composition may be used herein.

Additional Chassis Ingredients

Additional Structurant

The antiperspirant composition can further comprise an additional structurant. The additional structurant may be present in an amount from 1% to about 10%, by weight of the composition. The additional structurant(s) will likely be present at an amount less than the primary structurant.

Non-limiting examples of suitable additional structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; and solid triglycerides; behenyl alcohol, or combinations thereof.

Other non-limiting examples of additional structurants suitable for use herein are described in U.S. Pat. No. 5,976,514 (Guskey et al.) and U.S. Pat. No. 5,891,424 (Bretzler et al.).

Solvent

The antiperspirant composition of the present invention comprises a solvent at concentrations ranging from about 20% to about 80%, and more specifically from about 30% to about 70%, by weight of the composition. The solvent can be a volatile silicone which may be cyclic or linear.

"Volatile silicone" as used herein refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976), which descriptions are incorporated herein by reference.

The volatile silicone can be a cyclic silicone having from 3 to 7, and more specifically from 5 to 6, silicon atoms, and still more specifically 5, like cyclopentasiloxane. These cyclic silicone materials will generally have viscosities of less than about 10 centistokes at 25° C.

Linear volatile silicone materials suitable for use in the antiperspirant compositions include those represented by the formula:

wherein n is from 1 to 7, and more specifically from 2 to 3. These linear silicone materials will generally have viscosities of less than about 5 centistokes at 25° C.

Specific examples of volatile silicone solvents suitable for use in the antiperspirant compositions include, but are not limited to, Cyclomethicone D-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

Non-Volatile Organic Fluids

Non-volatile organic fluids may be present, for example, in an amount of about 15% or less, by weight of the composition.

Non-limiting examples of nonvolatile organic fluids include mineral oil, PPG-14 butyl ether, isopropyl myristate, petrolatum, butyl stearate, cetyl octanoate, butyl myristate, myristyl myristate, C12-15 alkylbenzoate (e.g., Finsolv.™.), octyldodecanol, isostearyl isostearate, octododecyl benzoate, isostearyl lactate, isostearyl palmitate, and isobutyl stearate.

Other Optional Ingredients

The anhydrous antiperspirant compositions of the present invention may further comprise any optional material that is known for use in antiperspirant and deodorant compositions or other personal care products, or which is otherwise suitable for topical application to human skin.

One example of an optional ingredient is a scent expression material. Scent expression or release technology may be employed with some or all of the fragrance materials to define a desired scent expression prior to use and during use of the antiperspirant products. Such scent expression or release technology can include cyclodextrin complexing material, like beta cyclodextrin. Other materials, such as, for example, starch-based matrices or microcapsules may be employed to "hold" fragrance materials prior to exposure to bodily-secretions (e.g., perspiration). The encapsulating material may have release mechanisms other than via a solvent; for example, the encapsulating material may be frangible, and as such, rupture or fracture with applied shear and/or normal forces encountered during application and while wearing. A microcapsule may be made from many materials, one example is polyacrylates.

Another example of optional materials are clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Talc, if used at higher levels can produce a significant amount of white residue which has been found to be a consumer negative for product acceptance. Therefore it is best to limit the composition to less than 10%, less than about 8%, less than about 6%, or less than about 3%, by weight of the composition.

Nonlimiting examples of other optional materials include emulsifiers, distributing agents, antimicrobials, pharmaceutical or other topical active, preservatives, surfactants, and so forth. Examples of such optional materials are described in U.S. Pat. No. 4,049,792 (Elsnau); U.S. Pat. No. 5,019,375 (Tanner et al.); and U.S. Pat. No. 5,429,816 (Hofrichter et al.); which descriptions are incorporated herein by reference.

Methods

Also included herein are methods. While some compositional attributes are listed below, the compositions included as part of the methods can have any combination of ingredients and attributes as described above.

One method is for enhancing fragrance expression and comprises formulating an antiperspirant composition so that no more than about 25%, by weight of the composition, of the non-perfume and non-antiperspirant ingredients have a polarity between about 3.0 $MPa^{1/2}$ and about 15 $MPa^{1/2}$. Further, the composition may comprise no more than about 20%, by weight of the composition, of non-perfume ingredients with a polarity of about 3.0 $MPa^{1/2}$ and about 15 $MPa^{1/2}$. The composition can have a hardness of 600 gram force or more. The composition may comprise a primary structurant, and antiperspirant active, a perfume, and additional chassis ingredients. The additional chassis ingredients may comprise an additional structurant, a solvent, a non-volatile organic fluid, or a combination thereof. The composition may further comprise other optional ingredients. The optional ingredients may comprise scent expression materials, clay mineral powders, pigments, emulsifiers, distributing agents, antimicrobials, pharmaceutical or other topical actives, preservatives, surfactants, or combinations thereof. The scent expression materials may comprise a fragrance complexing material, a microcapsule, or a combination thereof. The fragrance complexing material may comprise beta cyclodextrin. The microcapsule may comprise a polyacrylates microcapsule, a gelatin microcapsule, or a combination thereof.

An additional method can include a method of enhancing fragrance expression in a solid antiperspirant product, comprising formulating an antiperspirant composition comprising about 10 to about 20% of a primary structurant; about 10 to about 25% of an antiperspirant active; a perfume; and additional chassis ingredients; wherein about 15% or less, by weight of the composition, of the additional chassis ingredients have a polarity greater than about 3.0 $MPa^{1/2}$. The composition may further have 12%, 10, 8, 6, 5, 4, 3%, or less, by weight of the composition, of additional chassis ingredients with a polarity greater than about 3.0 $MPa^{1/2}$. The additional chassis ingredients may be selected from the group consisting of an additional structurant, a solvent, a non-volatile organic fluid, and combinations thereof. The composition can have a hardness of 600 gram force or more. The composition may further comprise other optional ingredients. The optional ingredients may comprise scent expression materials, clay mineral powders, pigments, emulsifiers, distributing agents, antimicrobials, pharmaceutical or other topical actives, preservatives, surfactants, or combinations thereof. The scent expression materials may comprise a fragrance complexing material, a microcapsule, or a combination thereof. The fragrance complexing material may comprise beta cyclodextrin. The microcapsule may comprise a polyacrylates microcapsule, a gelatin microcapsule, or a combination thereof.

EXAMPLES

Following are non-limiting inventive and comparative examples. Comparative Example 1 and Inventive examples 1-7 are made by adding all ingredients to a vessel, heating the vessel to 85° C., mixing for about 30 minutes at 85° C., cooling the composition to about 55-60° C., pouring it into a container (or multiple containers depending on size of the batch), and allowing it to cool to ambient temperature to solidify.

| Raw Materials | Comparative Formula #1 Weight % | Inventive Formula #1 Weight % |
|---|---|---|
| Aluminum Zirconium Trichlorohydrex Gly | 24.00 | 24.00 |
| Cyclopentasiloxane | 27.95 | 47.55 |
| C12-15 alkyl benzoate | 9.50 | — |
| PPG-14 Butyl ether | 6.50 | — |
| Mineral Oil | 1.00 | 2.00 |
| Phenyl Trimethicone | 3.00 | — |
| White Petrolatum, Super White Protopet | 3.00 | 3.50 |
| Stearyl Alcohol | 14.00 | 16.00 |
| Castor Wax | 3.85 | — |
| Ozokerite | — | 4.75 |
| Behenyl Alcohol | 0.20 | 0.20 |
| Cyclodextrin | 2.00 | — |
| Talc | 3.00 | — |
| Fragrance | 2.00 | 2.00 |

|  | Inventive Example 2 | Inventive Example 3 | Inventive Example 4 | Inventive Example 5 | Inventive Example 6 | Inventive Example 7 |
|---|---|---|---|---|---|---|
| Cyclopentasiloxane | 31.95% | 45.55% | 34.80% | 30.95% | 46.80% | 35.30% |
| Aluminum Zirconium Trichlorohydrex Glycine Powder | — | 24.00% | 24.00% | — | 24.00% | 24.00% |

-continued

|  | Inventive Example 2 | Inventive Example 3 | Inventive Example 4 | Inventive Example 5 | Inventive Example 6 | Inventive Example 7 |
| --- | --- | --- | --- | --- | --- | --- |
| Acid ZAG | 25.60% | — | — | 25.60% | — | — |
| Stearyl Alcohol (T) | 14.50% | 16.00% | 15.00% | 14.50% | 16.00% | 15.00% |
| Behenyl Alcohol (T, AC) | 0.20% | 0.20% | 0.20% | 0.20% | 0.20% | 0.20% |
| PPG-14 Butyl Ether (T, AC) | 2.00% | — | 2.00% | 2.00% | — | 2.00% |
| Petrolatum | 5.00% | 3.50% | 5.00% | 5.00% | 3.50% | 5.00% |
| Mineral Oil | 6.00% | 2.00% | 4.00% | 6.00% | 2.00% | 4.00% |
| Talc (T) | 3.00% | — | — | 3.00% | — | — |
| Dimethicone | 5.00% | — | 5.00% | 5.00% | — | 5.00% |
| Polyethylene synthetic wax | — | — | — | — | — | 3.50% |
| Ozokerite | 2.50% | 4.75% | 4.00% | 3.50% | 3.50% | — |
| Cyclodextrin | 3.00% | 2.00% | 4.00% | 3.00% | 2.00% | 4.00% |
| Max Perfume Level | 1.25% | 2.00% | 2.00% | 1.25% | 2.00% | 2.00% |
| Total RM | 100.00% | 100.00% | 100.00% | 100.00% | 100.00% | 100.00% |
| Total % of materials with polarity >3 MPa$^{1/2}$ | 19.7% | 16.2% | 17.2% | 19.7% | 16.2% | 17.2% |
| % of additional chassis materials with polarity >3 MPa$^{1/2}$ | 2.20% | 0.20% | 2.20% | 2.20% | 0.20% | 2.20% |

(T = having polarity above 3 MPa$^{1/2}$ and included in total % calculation; AC = having polarity above 3 MPa$^{1/2}$ and included in additional chassis calculation)

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The devices, apparatuses, methods, components, and/or compositions of the present invention can include, consist essentially of, or consist of, the components of the present invention as well as other ingredients described herein. As used herein, "consisting essentially of" means that the devices, apparatuses, methods, components, and/or compositions may include additional ingredients, but only if the additional ingredients do not materially alter the basic and novel characteristics of the claimed devices, apparatuses, methods, components, and/or compositions.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of enhancing fragrance expression in an antiperspirant composition, comprising the steps of adding the antiperspirant composition components comprising an antiperspirant active, a perfume, non-perfume ingredient, and a non-antiperspirant active ingredient, wherein no more than 17% by weight of the antiperspirant composition, of the non-perfume and non-antiperspirant active ingredients, have a polarity between about 3 MPa$^{1/2}$ and 15 MPa$^{1/2}$, into a vessel, heating the vessel, mixing the composition, and then cooling the composition;
   wherein the antiperspirant composition comprises 11% to 15% of a non-volatile organic fluid;
   and wherein the antiperspirant composition is anhydrous.

2. The method of claim 1, wherein the antiperspirant composition comprises less than 4%, by weight of the antiperspirant composition of non-perfume and non-antiperspirant ingredients with a polarity of 15 MPa$^{1/2}$ or more.

3. The method of claim 1, wherein the antiperspirant composition comprises less than 2%, by weight of the antiperspirant composition of non-perfume and non-antiperspirant ingredients with a polarity of 15 MPa$^{1/2}$ or more.

4. The method of claim 1, wherein the antiperspirant composition is substantially free of castor wax.

5. The method of claim 1, wherein the antiperspirant composition has a hardness of about 600 gram force or more.

6. The method of claim 1, wherein the antiperspirant composition comprises no more than 15%, by weight of the antiperspirant composition, of non-perfume and non-antiperspirant ingredients with a polarity of between $3.0\ \mathrm{MPa}^{1/2}$ and $15\ \mathrm{MPa}^{1/2}$.

7. The method of claim 1, wherein the non-perfume and non-antiperspirant ingredients are selected from the group consisting of primary structurant, additional chassis ingredients, other optional ingredients, and combinations thereof.

8. The method of claim 7, wherein the additional chassis ingredients comprise an additional structurant, a solvent, a non-volatile organic fluid, or combinations thereof.

9. The method of claim 7, wherein the other optional ingredients comprise a fragrance complexing material, a microcapsule, or a combination thereof.

10. The method of claim 9, wherein the fragrance complexing material comprises beta cyclodextrin.

11. The method of claim 9, wherein the microcapsule comprises a polyacrylate microcapsule, a gelatin microcapsule, or a combination thereof.

* * * * *